(12) United States Patent
Reibel et al.

(10) Patent No.: US 10,624,985 B2
(45) Date of Patent: Apr. 21, 2020

(54) BIORESORBABLE NONWOVEN FABRIC MADE OF GELATIN

(75) Inventors: Denis Reibel, Herrlisheim (FR); Claudio Walter, Heppenheim (DE); Bernd Altmueller, Birkenau (DE)

(73) Assignee: CARL FREUDENBERG KG, Weinheim (DE)

( * ) Notice: Subject to any disclaimer, the term of this patent is extended or adjusted under 35 U.S.C. 154(b) by 1561 days.

(21) Appl. No.: 12/678,219

(22) PCT Filed: Sep. 17, 2008

(86) PCT No.: PCT/EP2008/007757
§ 371 (c)(1),
(2), (4) Date: Jul. 2, 2010

(87) PCT Pub. No.: WO2009/036958
PCT Pub. Date: Mar. 26, 2009

(65) Prior Publication Data
US 2010/0285291 A1 Nov. 11, 2010

(30) Foreign Application Priority Data

Sep. 18, 2007 (DE) .................. 10 2007 044 648

(51) Int. Cl.
*D04H 13/00* (2006.01)
*B32B 5/00* (2006.01)
(Continued)

(52) U.S. Cl.
CPC ............... *A61L 15/46* (2013.01); *A61L 15/32* (2013.01); *D01D 5/18* (2013.01); *D01F 1/10* (2013.01); *D01F 4/00* (2013.01); *D01F 9/00* (2013.01); *D04H 1/02* (2013.01); *D04H 1/4266* (2013.01); *D04H 1/4382* (2013.01); *D04H 1/70* (2013.01); *D04H 1/728* (2013.01); *D04H 1/736* (2013.01);
(Continued)

(58) Field of Classification Search
None
See application file for complete search history.

(56) References Cited

U.S. PATENT DOCUMENTS 3,757,004 A 9/1973 Brown et al.
6,596,048 B1 7/2003 Tuffal et al.
(Continued)

FOREIGN PATENT DOCUMENTS

CA 2427752 A1 5/2002
CN 1270240 A 10/2000
(Continued)

OTHER PUBLICATIONS

Electrospun Gelatin Fibers: Effect of Solvent System on Morphology and Fiber Diameters. Nuanchan Choktaweesap, et al. Polymer Journal, vol. 39, No. 6, pp. 622-631 (2007).*
(Continued)

*Primary Examiner* — Marla D McConnell
*Assistant Examiner* — Kevin Worrell
(74) *Attorney, Agent, or Firm* — Leydig, Voit & Mayer, Ltd.

(57) ABSTRACT

A nonwoven fabric includes fibers of a fiber raw material including gelatin, the fibers including at least one of an antimicrobially effective substance and an antibiotic, wherein the fibers are produced by rotational spinning.

26 Claims, 4 Drawing Sheets

(51) Int. Cl.

| | | |
|---|---|---|
| *B29C 47/00* | (2006.01) | |
| *A61L 15/46* | (2006.01) | |
| *A61L 15/32* | (2006.01) | |
| *D04H 1/736* | (2012.01) | |
| *D04H 1/4266* | (2012.01) | |
| *D04H 1/02* | (2006.01) | |
| *D04H 3/016* | (2012.01) | |
| *D04H 1/4382* | (2012.01) | |
| *D01F 9/00* | (2006.01) | |
| *D04H 3/00* | (2012.01) | |
| *D01F 4/00* | (2006.01) | |
| *D04H 1/728* | (2012.01) | |
| *D01D 5/18* | (2006.01) | |
| *D04H 3/03* | (2012.01) | |
| *D01F 1/10* | (2006.01) | |
| *D04H 1/70* | (2012.01) | |

(52) U.S. Cl.
CPC .............. *D04H 3/00* (2013.01); *D04H 3/016* (2013.01); *D04H 3/03* (2013.01); *A61L 2300/104* (2013.01); *A61L 2300/404* (2013.01); *A61L 2300/406* (2013.01); *A61L 2300/414* (2013.01); *Y10T 442/696* (2015.04)

(56) References Cited

U.S. PATENT DOCUMENTS

| | | | |
|---|---|---|---|
| 7,005,556 B1* | 2/2006 | Becker et al. | 602/48 |
| 7,118,698 B2 | 10/2006 | Armantrout et al. | |
| 8,124,826 B2 | 2/2012 | Addison et al. | |
| 2003/0161995 A1* | 8/2003 | Kauschke et al. | 428/138 |
| 2004/0001880 A1 | 1/2004 | Bowler et al. | |
| 2004/0073295 A1 | 4/2004 | Chaikof et al. | |
| 2004/0076661 A1* | 4/2004 | Chu et al. | 424/443 |
| 2004/0110439 A1 | 6/2004 | Chaikof et al. | |
| 2005/0101900 A1 | 5/2005 | Qin et al. | |
| 2005/0287320 A1* | 12/2005 | Dalton et al. | 428/34.1 |
| 2006/0068013 A1* | 3/2006 | DiTizio et al. | 424/484 |
| 2006/0115805 A1* | 6/2006 | Hansen et al. | 435/4 |
| 2007/0207186 A1* | 9/2007 | Scanlon et al. | 424/424 |
| 2007/0248640 A1* | 10/2007 | Karabey et al. | 424/423 |
| 2007/0286895 A1 | 12/2007 | Bowler et al. | |
| 2009/0220579 A1 | 9/2009 | Hassingboe et al. | |

FOREIGN PATENT DOCUMENTS

| | | | |
|---|---|---|---|
| CN | 1961974 A | * | 5/2007 |
| CN | 1978718 A | | 6/2007 |
| DE | 60026510 T2 | | 10/2006 |
| DE | 102005048939 A1 | | 1/2007 |
| GB | 862428 A | | 3/1961 |
| JP | 2001123397 A | | 5/2001 |
| JP | 2002518282 A | | 6/2002 |
| JP | 2003278062 A | | 10/2003 |
| JP | 2004525268 A | | 8/2004 |
| JP | 2005163204 A | | 6/2005 |
| JP | 2005195438 A | | 7/2005 |
| JP | 2005537823 A | | 12/2005 |
| JP | 2006188811 A | | 7/2006 |
| JP | 2006522240 A | | 9/2006 |
| JP | 2007511313 A | | 5/2007 |
| WO | WO 0067694 A1 | | 11/2000 |
| WO | WO 2004002384 A1 | | 1/2004 |
| WO | WO 2005054553 A1 | | 6/2005 |
| WO | WO 2007122232 A2 | | 11/2007 |

OTHER PUBLICATIONS

International Search Report for PCT/EP2008/007757 dated Dec. 23, 2009.

Yang et al., Preparation of gelatin/PVA nanofibers and their potential application in controlled release of drugs, Carbohydrate Polymers, 2007, vol. 69, S. 538-543, State Key Laboratory of Chemical Resource Engineering, College of Material Science and Engineering, Beijing University of Chemical Technology, Beijing 100029, China, Sep. 27, 2006.

* cited by examiner

BIORESORBABLE NONWOVEN FABRIC MADE OF GELATIN

This application is a U.S. National Phase Application under 35 U.S.C. § 371 of International Application No. PCT/EP2008/007757, filed on Sep. 17, 2008, which claims benefit to German Patent Application No. 10 2007 044 648.0, filed on Sep. 18, 2007. The International Application was published in German on Mar. 26, 2009, as WO 2009/036958 under PCT Article 21 (2).

The invention relates to a nonwoven fabric comprising fibers of a fiber raw material which comprises gelatin, the fibers having been provided with an antimicrobial effective substance and/or an antibiotic. The invention also relates to a rotational spinning method for the production of the nonwoven fabric.

BACKGROUND

Such nonwoven fabrics are already known from the prior art. In particular, WO 2004/002384 A1 describes a nonwoven fabric which comprises silver and is used as a wound dressing. Polyurethanes or polyacrylates are proposed as fiber material there.

Nonwoven fabrics are frequently used for medical applications. A sufficient tensile strength to enable them to be used as dressing material is imparted to the webs present as raw material for the nonwoven fabrics by water-jet bonding or thermal or chemical bonding.

The mechanical or chemical bonding methods, however, can adversely affect the antimicrobial or antibiotic treatment of the fibers, namely inhibit the action of the active substances or even partly detach them from the fibers. Complicated and expensive aftertreatment steps are therefore frequently required in order to bring the consolidated nonwoven fabrics into a state suitable for use.

Furthermore, the fact that fiber raw material comprising polymers which permit sufficient bonding is frequently not tolerated by wounds, in particular is not bioresorbable, is disadvantageous.

SUMMARY OF THE INVENTION

An aspect of the present invention is to produce a bioresorbable nonwoven fabric with sufficient strength in an economical manner.

According to this, a nonwoven fabric mentioned at the outset is characterized in that the fibers are produced by a rotational spinning method.

According to the invention, it has been recognized that gelatin is a biodegradable material which can surprisingly readily be laid to give a web. Furthermore, it was recognized that the fibers of the non-woven, partially without phase boundary, penetrate into each other, network with each other, and thereby form a continuous network. The resulting nonwoven fabric surprisingly shows, without further bonding measures, a sufficiently high tensile strength to be used as dressing material or wound dressing. The antimicrobially effective substance and/or the antibiotic are not adversely affected in their action by bonding measures. It has further been recognized that the diameter of the fibers can be established in a narrow distribution by means of a rotational spinning method. Fibers having a diameter of on average from 0.3 to 500 µm, on average from 3 to 200 µm and even on average from 5 to 100 µm can be produced by the rotational spinning method, which fibers form a network with one another, partially through the gelatin. The narrow distribution of the diameter of the fibers permits a homogeneous and stable structure of the nonwoven fabric without expensive additional bonding measures.

Some fibers could be twisted or interlaced with one another or could have a twisted structure. The twistings or interlacings are surprisingly established during the rotational spinning and additionally promote the strength and the stretching behavior of the nonwoven fabric.

Some fibers could be interlaced with one another and form one or more fiber bundles. Through the interlacings of individual fibers, these are combined into fiber bundles and could be reversibly displaced relative to one another. As a result of this, it is possible to stretch the nonwoven fabric without destruction. During the stretching, individual fibers are in fact pulled and are displaced relative to other fibers. The twistings and interlacings even promote the return of the fibers to their position prior to stretching. The nonwoven fabric therefore shows high dimensional stability.

The fibers could be produced exclusively from gelatin or derivatives of gelatin, an antimicrobial substance and/or an antibiotic being present in and/or on the fibers. Such a nonwoven fabric can be degraded by the chemistry of the human body and is therefore virtually completely bioresorbable. This nonwoven fabric can be introduced into the human body.

The antimicrobially effective substance and/or the antibiotic could be homogeneously distributed in the fibers. As a result of this, gradual release of the substance and/or of the antibiotic with a long-lasting effect can be established.

The antimicrobially effective substance and/or the antibiotic could be present in the fibers at the nanoscale level. Nanoscale structures are understood as meaning regions of any morphology which have dimensions in the nanometer range at least in one direction in space. As a result of this, the antimicrobially effective substance or the antibiotic acquires high mobility. An antimicrobial substance present at the nanoscale level shows particularly high reactivity if the substance is brought into contact with bacteria, viruses, fungi or spores. Furthermore, the nonwoven fabric releases the active substance very easily to media which come into contact with it. To this extent, the nonwoven fabric is distinguished by a high release capacity with respect to the antimicrobially effective substance and/or the antibiotic.

The antimicrobially effective substance and/or the antibiotic could be distributed on the fibers. This permits spraying of the nonwoven fabric with the substance and/or the antibiotic in order to ensure fast release to the human body.

The antimicrobially effective substance could contain silver. Silver is particularly suitable as an antimicrobially active substance since it is virtually nontoxic for humans. Furthermore, silver has relatively low allergenic potential. Silver acts as an antiseptic substance in low concentrations over a long period on a multiplicity of infectious germs. Most known bacteria moreover show no resistance to silver.

The substance could comprise at least one subgroup element. Subgroup elements are distinguished by an antimicrobial effect. Against this background, it is conceivable that a plurality of subgroup elements are present together in order selectively to fight different bacterial species. It has been found in experimental series that there is a ranking of substances used with respect to the antimicrobial efficacy. This may be represented as follows. Silver is the most effective substance, followed by mercury, copper, cadmium, chromium, lead, cobalt, gold, zinc, iron and finally manganese. Against this background, it is conceivable also to use main group elements which show an antimicrobial effect. The antimicrobially effective substance could comprise a gold-silver mixture or exclusively consist of a gold-silver mixture. Mixtures of this type show particularly high antimicrobial efficacy. It has surprisingly been found that the presence of gold further increases the antimicrobial effect.

At least part of the fibers could be in the form of nanofibers. A nonwoven fabric of this form can be made particularly light and thin.

The nonwoven could have a tensile strength, at a specific weight per unit area of from 140 to 180 g/m2, in the dry state, of 0.15 N/mm2 or more and an elongation at break in the hydrated state of 150%, preferably of 200% or more. Such a nonwoven fabric is particularly suitable as dressing material since it can be rolled up without problems.

The nonwoven fabric could have an open pore structure having an air permeability of 0.5 l/min*cm2, this parameter being determined according to DIN 9237. Such a nonwoven fabric is particularly suitable as dressing material since it enables the skin to release moisture and to breathe.

In order to avoid repetitions with regard to the inventive step, reference may be made to the statements regarding the nonwoven fabric as such.

The emergent fibers could be guided in a direct manner without contact. Noncontact and defined guidance of the fibers before they encounter a laying device permits a modification of the fibers. Thus, the duration of guidance and the direction of guidance alone can influence the fiber length, the fiber diameter and the fiber structure. Directed noncontact guidance produces a more homogeneous fiber spectrum than a production process without guidance. Very specifically, the width of a distribution curve of all fiber properties can be established by the guidance alone. As a result of this, the quantity of fibers having an undesired fiber geometry can be considerably reduced.

In a configuration of particularly advantageous design, the fibers could be guided by a suction device. It is conceivable for the fibers to be transported by a gas stream. If the gas stream is laminar, the fibers can be stretched and shaped between the laminar layers.

Air could act as the gas. Air is an economical gas which is distinguished in that a production process could be carried out at atmospheric pressure. It is also conceivable to use further gases, in particular inert gases, such as nitrogen, instead of air. This ensures that fiber raw material which comprises reactive groups or tends to secondary reactions after leaving the container can be processed.

It would be possible to produce fibers which have a diameter of from 0.3 to 500 μm. To this extent, production of nanofibers is possible without an electrostatic field having to be used.

The exit regions of the container could be configured as passages. It is conceivable here for the passages to be circular, oval or rectangular. Depending completely on the shape of the passages, the fiber geometry can be influenced.

The passages could have a diameter or a width of up to 500 μm. This dimensioning has proven to be particularly advantageous for the production of nanofibers and microfibers. The passages could be positioned at a distance of one centimeter apart from one another. It is also conceivable for the passages to be arranged in a plurality of rows one on top of the other. This makes it possible to increase the throughput of fiber raw material in a particularly simple manner. By reducing or increasing the diameter, it is also possible to produce nanofibers or microfibers in the range from 0.3 to 500 μm.

The container could be rotatable at up to 25000 revolutions per minute. This high rotational speed makes it possible to produce nanofibers having a diameter of not more than 100 nm. Usually, nanofibers are produced by an electrical spinning method with the use of an electric field. By a suitable design of the container and very high rotational speeds, however, it is possible to produce nanofibers without an electric field. Fibers having a relatively large diameter can also be produced through the choice of the rotational speed and viscosity of the fiber raw material.

The container could be capable of being heated to 300° C. This configuration advantageously permits use of virtually all thermoplastic fiber-forming materials as fiber raw material. It is conceivable here that polyesters, polyamides, polyurethanes, polylactides and polyhydroxybutyrate/polyhydroxyvalerate copolymers and natural sugars, e.g. sucrose, or mixtures of said substances, are used. In addition, the fiber raw material could comprise polyolefins or reactive polymers. It is conceivable here that polypropylene, polypropylene grafted with acrylic acid and/or modified polypropylene are used. The use of biodegradable substances, such as gelatin, as fiber raw material permits the production of fibers which can be disposed of without problems. Furthermore, medical products such as wound dressings or cell growth media can be produced with these fibers. All substances mentioned can be used alone or as a mixture with others as fiber raw material.

A laying device for accepting fiber raw material could be associated with the rotating container. The laying device could be in the form of a platform on which the fibers for the formation of a fiber gaze or web can be laid. It is also conceivable for the laying device to be a rotating device on which fibers for coating a cylindrical body or for producing a wound web are taken up.

An electrical potential difference could exist between the laying device and the container. This specific configuration permits the production of electrostatically charged fibers.

Furthermore, it is conceivable for the electrical potential difference to be used for supporting the production of nanofibers. Here, the effects of the centripetal forces and of the electric field are additive, i.e the fiber raw material is firstly spun by the centripetal forces in thin filaments tangentially away from the rotating container and furthermore are optionally even further split up by the electric field. To this extent, it is conceivable to realize a production process by means of which fibers in the subnanometer range can be produced.

The fiber raw material could already be introduced in fluidized form into the container. This makes it possible to carry out a continuous process by in fact heating the fiber raw material outside the container. However, it is also conceivable to fluidize the fiber raw material only after it has been introduced into the container.

Nonwoven fabrics of the type described here could be used in the medical sector since they are very readily modifiable with regard to their fabric structure and material composition. For example, it is conceivable to adjust the fabric structure so that they can act as wound dressing if in fact the fiber fabric structure can readily intergrow with the human tissue. Further medical applications, such as the use as a cell growth media, are conceivable.

The nonwoven fabric described here is suitable in particular for production of a cotton swab or swab since it is sufficiently stable and has a disinfectant effect.

Further treatments of the nonwoven fabric are possible. The nonwoven fabric could be provided with recombinant growth factors, autologous growth factors, in particular platelet preparations, adhesion factors, in particular RDG peptides, and/or autologous cell preparations, in particular bone marrow aspirates.

There are now various possibilities for configuring and further developing the teaching of the present invention in an advantageous manner. For this purpose, reference should be made firstly to the following claims and secondly to the following explanation of preferred working examples of the nonwoven fabric according to the invention, with reference to the drawing.

In conjunction with the explanation of the preferred working examples with reference to the drawing, in general preferred configurations and further developments of the teaching are also explained.

DETAILED DESCRIPTION

Working Example 1

Figure 1:
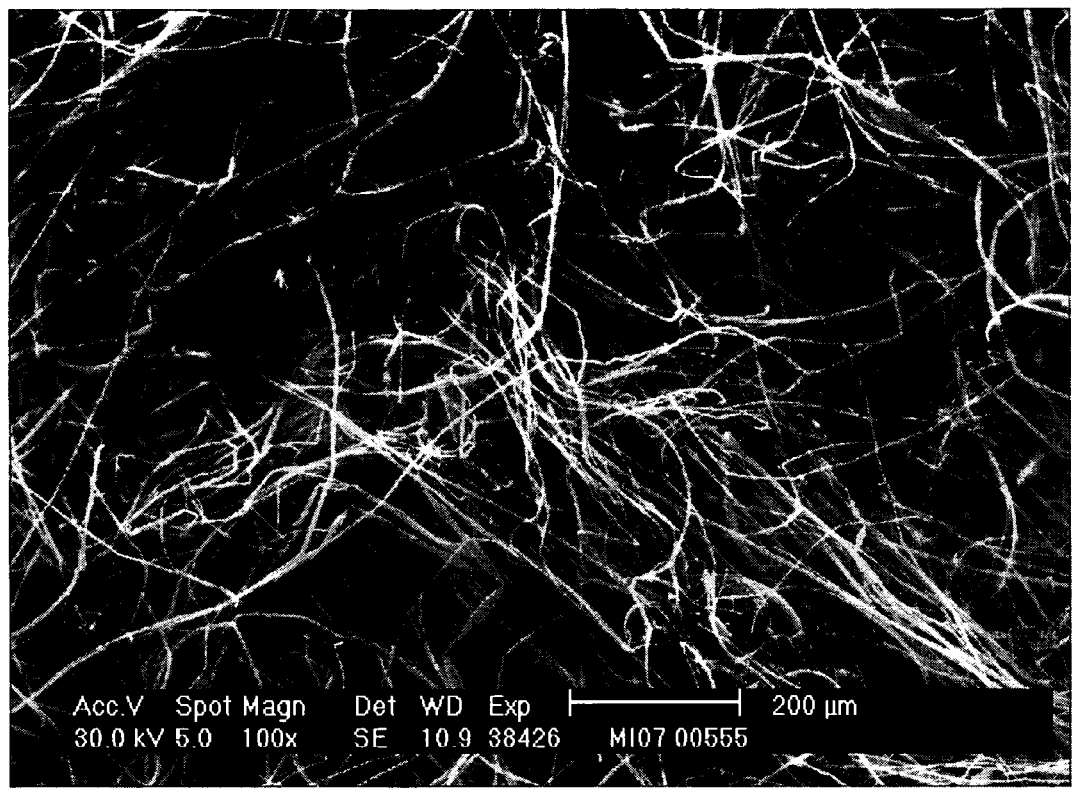
FIG. 1 shows an SEM picture of a nonwoven fabric comprising gelatin, in whose fibers silver is distributed as antimicrobial substance in the form of nanoscale particles.
Figure 2:
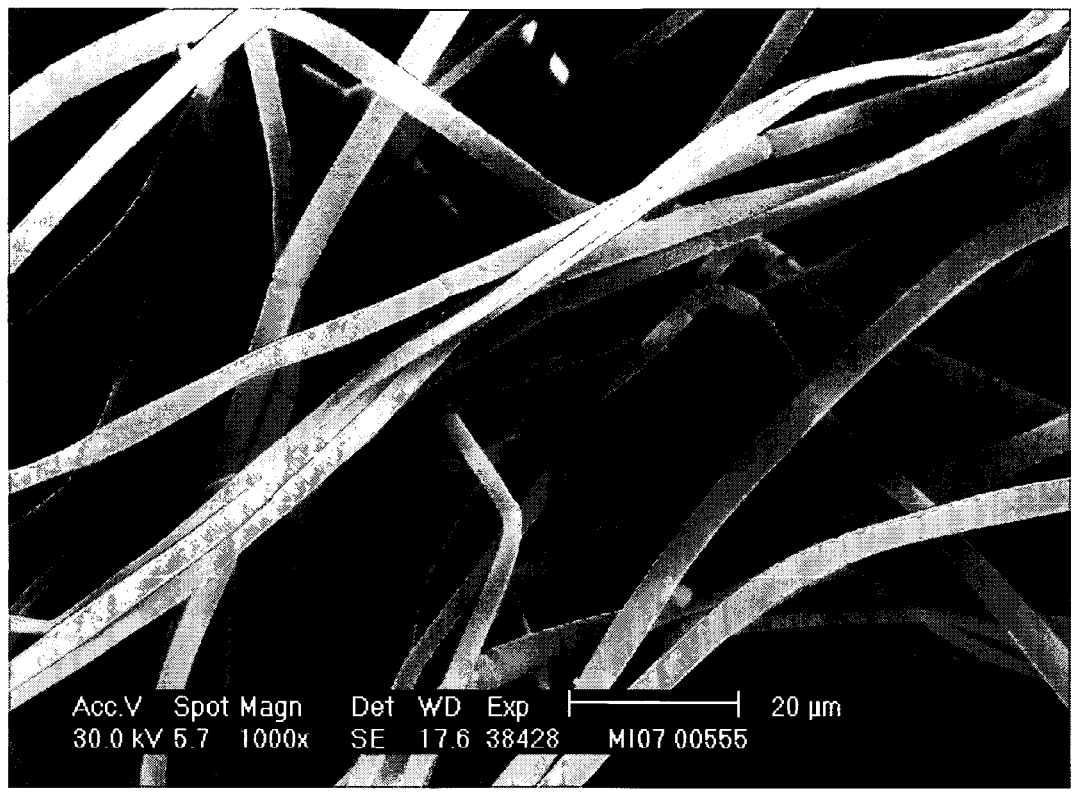
FIG. 2 shows an SEM picture of the nonwoven fabric from FIG. 1 in magnified view.

A nonwoven fabric comprising silver as an antimicrobial substance according to FIGS. 1 and 2 is produced by a rotational spinning method as follows:

First, a 20% strength gelatin solution is prepared. A gelatin of type A PIGSKIN from Gelita AG is used. The gelatin is stirred into water. 1000 ppm of the solids content of a 5% strength aqueous silver solution which contains silver in the form of nanoscale particles are added to the gelatin solution. A silver solution from RENT A SCIENTIST, of the type AGPURE was used. This results in a final concentration of 50 mg of silver/(kg of gelatin solution).

The gelatin solution then remains standing for about one hour in order to swell. Thereafter, the gelatin solution is dissolved in an ultrasonic bath at 60° C. and then kept at a temperature of 80-85° C. for about 2 hours. In the gelatin solution, the particles of silver can form agglomerates which are dissolved by stirring the gelatin solution. The gelatin solution thermostatted at 80-85° C. is fed by means of a peristaltic pump as fiber raw material into the container of an apparatus for rotational spinning according to DE 102005048939 A1.

The container has a temperature of about 120° C. and rotates at a rotational speed of 4500 rpm. Cut-outs which are configured as holes having a diameter of 0.3 mm are present in the container. The fiber raw material is forced through the cut-outs by the centripetal force and spun into fibers which are stretched by a suction device. The suction device is present below the container.

After the gelatin has formed a network, an antimicrobially effective bioresorbable nonwoven fabric comprising gelatin, namely a gelatin nonwoven fabric, is obtained.

Figure 3:
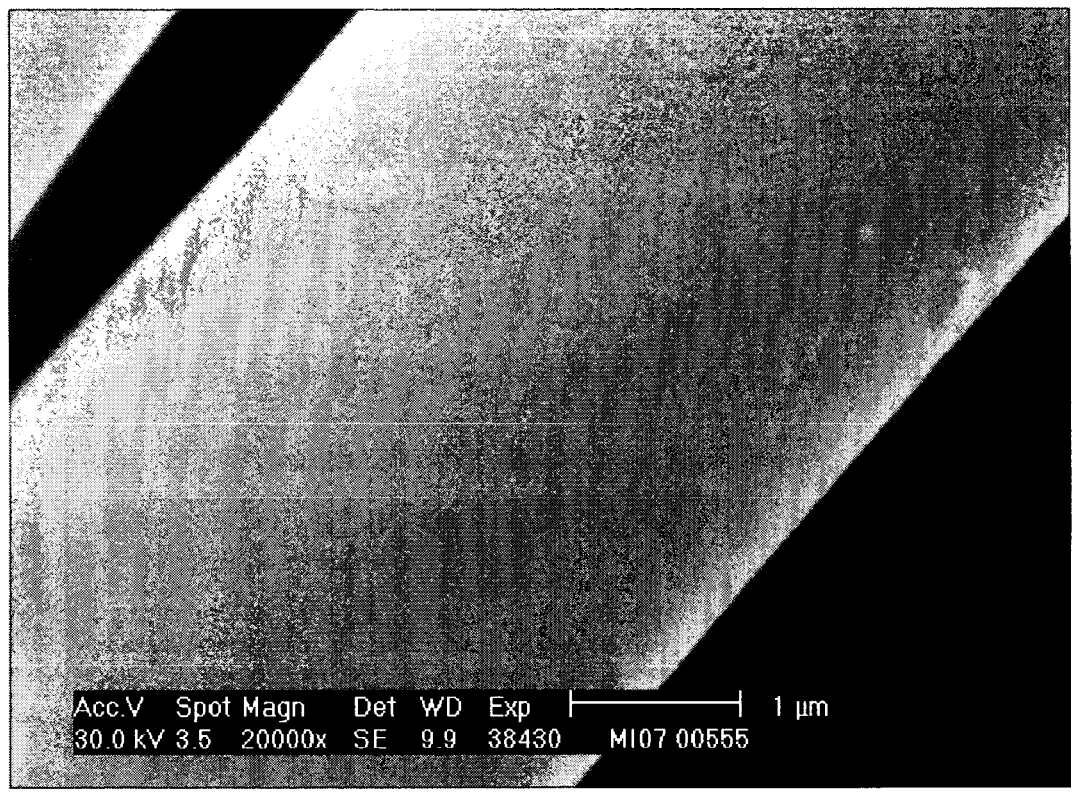
FIG. 3 shows an SEM picture of a fiber of the nonwoven fabric from FIG. 1, in magnified view, which has a diameter of 4 µm.

The nonwoven fabric was characterized by means of a scanning electron microscope (SEM). FIGS. 1 to 3 show SEM pictures of the nonwoven fabric described here, at different magnifications. According to a characterization based on ICP (according to EN ISO 11885), the silver concentration in the nonwoven fabric is 44 mg/kg.

In FIG. 2, it is evident, particularly in the lower left quarter of the figure, that some fibers are interlaced or twisted with one another. The occurrence of these interlacings is characteristic of a nonwoven fabric which is produced by a rotational spinning method.

Working Example 2

A nonwoven fabric comprising antibiotics is produced by a rotational spinning method as follows:

For the production of a nonwoven fabric, first a 20% strength gelatin solution is prepared. A gelatin of the type A PIGSKIN according to example 1 is used. The gelatin is stirred into water. This gelatin solution remains standing for one hour in order to swell. Thereafter, the gelatin solution is dissolved in an ultrasonic bath at 60° C. and then kept at a temperature of 80-85° C. for about two hours.

The gelatin solution thermostatted at 80-85° C. is fed by means of a peristaltic pump into the container according to DE 102005048939 A1. Shortly before the gelatin solution enters the cut-outs, an ampoule of gentamicin solution (GENTAMICIN 40 from HEXAL AG) is mixed with the gelatin solution. The container has a temperature of about 120° C. and rotates at a rotational speed of 4500 rpm. The fiber raw material is forced out of the cut-outs present on the container by the centripetal force and is spun into fibers. The fibers are stretched by a suction device which is present below the container. After the gelatin has formed a network, a nonwoven fabric having an enclosed antibiotic which has an antimicrobiotic action and at the same time is bioresorbable is obtained.

Working Example 3

A nonwoven fabric with subsequent antibiotic treatment is produced by a rotational spinning method as follows:

For the production of a nonwoven fabric, first a 20% strength gelatin solution is prepared. A gelatin of the type A PIGSKIN according to example 1 is used. The gelatin is stirred into water. This gelatin solution remains standing for one hour in order to swell.

Thereafter, the gelatin solution is dissolved in an ultrasonic bath at 60° C. and then kept at a temperature of 80-85° C. for about two hours.

The gelatin solution thermostatted at 80-85° C. is fed by means of a peristaltic pump into the container according to DE 102005048939 A1. The container has a temperature of 120° C. and rotates at a rotational speed of 4500 rpm. The fiber raw material is forced out of the cut-outs present on the container by the centripetal force and is spun into fibers. The fibers are stretched by a suction device which is present below the container. After the gelatin has formed a network, the nonwoven fabric is sprayed with a solution of gentamicin and then dried.

Figure 4:
FIG. 4 shows an SEM picture of a fiber bundle which comprises fibers interlaced with one another.

FIG. 4 shows a nonwoven fabric which was produced analogously to working example 1. In the case of this nonwoven fabric, some fibers are interlaced with one another and form a fiber bundle. As a result of the interlacing of individual fibers, they are combined to form a fiber bundle and may be reversibly displaced relative to one another. This makes it possible to stretch the nonwoven fabric without destruction. During the stretching, individual fibers are in fact pulled and are displaced relative to other fibers. The twistings or interlacings even promote the return of the fibers to their position prior to stretching. The nonwoven fabric therefore shows high dimensional stability.

Regarding further advantageous configurations and further developments of the teaching according to the invention, reference is made firstly to the general part of the description and secondly to the attached patent claims. Finally, it should be very particularly emphasized that the working examples chosen purely randomly above serve merely for discussing the teaching according to the invention but do not limit said teaching to these working examples.

The invention claimed is:

1. A nonwoven fabric, comprising:
   fibers of a fiber raw material consisting essentially of at least one gelatin or derivative of gelatin,
   wherein the fibers comprise an antimicrobially effective substance, an antibiotic, or a mixture of two or more of any of these,
   wherein the fibers have a diameter from 0.3 to 500 μm,
   wherein the fibers are produced by rotational spinning of the fiber raw material, then drawing spun fiber raw material through circular, oval, or rectangular passages, then guiding discharged fibers from the passages in a directed and non-contacting manner,
   wherein at least some of the fibers are twisted with one another, interlaced with one another, or have a twisted structure, so as to bond to one another as laid without further bonding measures,
   wherein the fabric has an open pore structure and an air permeability of at least 0.5 L/min·cm$^2$.

2. The nonwoven fabric as recited in claim 1, wherein at least some of the fibers are interlaced with one another and form at least one fiber bundle.

3. The nonwoven fabric as recited in claim 1, wherein the fibers consist of:
   the at least one gelatin or derivative of gelatin; and
   the antimicrobial substance, the antibiotic, or the mixture.

4. The nonwoven fabric as recited in claim 1, wherein the antimicrobially effective substance, the antibiotic, or the mixture
   is homogenously distributed in the fibers, and/or
   present in the fibers at a nanoscale level, and/or
   distributed on the fibers.

5. The nonwoven fabric as recited in claim 1, wherein the antimicrobially effective substance is present and comprises silver.

6. The nonwoven fabric as recited in claim 1, further comprising:
   nanofibers, comprising gelatin and/or a gelatin derivative, having a diameter of not more than 100 nm, which nanofibers are not electrically spun.

7. The nonwoven fabric as recited in claim 1, wherein the fabric has a tensile strength of at least 0.15 N/mm$^2$ at a specific weight per unit area from 140 to 180 g/m$^2$ in a dry state, and
   wherein the fabric has an elongation at break in a hydrated state of 150% to 200%.

8. A method for producing the nonwoven fabric of claim 1, the method comprising:
   introducing the fiber raw material into a container;
   introducing the antimicrobially effective substance, the antibiotic, or the mixture into the container;
   rotating the container so as to fluidize the fiber raw material and discharge the fluidized fiber raw material from the container by centripetal forces so as to form the fibers; and
   joining the fibers together in a nonwoven manner to provide the nonwoven fabric.

9. The method as recited in claim 8, further comprising:
   guiding the fibers being discharged from the container in a directed and non-contacting manner.

10. The method as recited in claim 9, wherein the guiding is performed using a suction device.

11. The method as recited in claim 8, wherein the fluidized fiber raw material is discharged through passages having a diameter of up to 500 μm.

12. The method as recited in claim 8, wherein the rotating is carried out at a speed of up to 25,000 revolutions per minute.

13. The method as recited in claim 8, wherein the container can be heated to a temperature of 300° C.

14. The method as recited in claim 8, further comprising:
    laying the fibers on a laying device,
    wherein an electrical potential difference exists between the laying device and the container.

15. The method as recited in claim 8, further comprising:
    contacting the nonwoven fabric with a drug suitable for wound healing.

16. The method as recited in claim 8, further comprising:
    disposing the nonwoven fabric onto an end of a rod element so as to form a swab.

17. A method for producing the nonwoven fabric of claim 1, the method comprising:
    rotating a container comprising the fiber raw material in fluidized form, thereby discharging the fluidized fiber raw material from the container by centripetal forces so as to form the fibers;
    joining the fibers together to provide the nonwoven fabric; and
    disposing the antimicrobially effective substance, the antibiotic, or the mixture on the fibers.

18. A swab, comprising:
    a rod element; and
    the nonwoven fabric of claim 1,
    wherein the nonwoven fabric is disposed onto an end of the rod element.

19. The nonwoven fabric as recited in claim 1, wherein the fibers are made by a process that comprises fluidizing gelatin in a solution comprising water.

20. The nonwoven fabric as recited in claim 5, wherein the antimicrobially effective substance further comprises gold.

21. A nonwoven fabric, comprising:
    fibers substantially comprising gelatin; and
    an antimicrobially effective substance, an antibiotic, or a mixture of two or more of any of these,
    wherein the fibers have a diameter from 0.3 to 500 μm,
    wherein at least some of the fibers are twisted or interlaced so as to bond to one another as laid without further bonding measures, and wherein the fabric has an air permeability of at least 0.5 L/min·cm$^2$.

22. The nonwoven fabric as recited in claim 21, further comprising:
    nanofibers, substantially comprising gelatin, having a diameter of not more than 100 nm, which nanofibers are not electrically spun.

23. The nonwoven fabric as recited in claim 21, wherein the fabric has a tensile strength of at least 0.15 N/mm$^2$ at a specific weight per unit area from 140 to 180 g/m$^2$ in a dry state, and
    wherein the fabric has an elongation at break in a hydrated state of 150% to 200%.

24. A nonwoven fabric, comprising:
    fibers substantially comprising gelatin, a gelatin derivative, or a mixture of two or more of these; and an antimicrobially effective substance, an antibiotic, or a mixture of two or more of any of these,
wherein the fibers have a diameter up to 500 µm, and
wherein the fibers are rotationally spun, and some of the fibers are twisted or interlaced so as to bond to one another without further bonding measures, and wherein the fabric has an air permeability of at least 0.5 L/min·cm$^2$.

25. The nonwoven fabric as recited in claim 1, wherein the fabric has a tensile strength of at least 0.15 N/mm$^2$ at a specific weight per unit area from 140 to 180 g/m$^2$ in a dry state, and
wherein the fabric has an elongation at break in a hydrated state of 150% to 200%.

26. The nonwoven fabric as recited in claim 24, wherein the fibers comprising nanofibers having a diameter of not more than 100 nm, which nanofibers are not electrically spun.

\* \* \* \* \*